(12) United States Patent
Fukuda et al.

(10) Patent No.: US 6,322,581 B1
(45) Date of Patent: Nov. 27, 2001

(54) SUTURING NEEDLE FOR MEDICAL USE

(75) Inventors: Masatoshi Fukuda; Masaaki Matsutani, both of Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 0 days.

(21) Appl. No.: 09/644,745

(22) Filed: Aug. 24, 2000

(30) Foreign Application Priority Data

Aug. 26, 1999 (JP) .................................................. 11-239653

(51) Int. Cl.$^7$ .................................................. A61B 17/06
(52) U.S. Cl. ........................................... 606/223; 606/222
(58) Field of Search ..................... 606/222–227, 606/223

(56) References Cited

U.S. PATENT DOCUMENTS

| | | | |
|---|---|---|---|
| 1,599,059 | * 9/1926 | Morton | 606/223 |
| 2,516,710 | * 7/1950 | Maszolo | 606/223 |
| 3,160,157 | * 12/1964 | Chrisman | 606/223 |
| 3,197,997 | * 8/1965 | Kurtz | 606/223 |
| 4,524,771 | * 6/1985 | McGregor et al. | 606/223 |
| 4,932,961 | * 6/1990 | Wong et al. | 606/223 |
| 5,002,564 | * 3/1991 | McGregor et al. | 606/223 |
| 5,269,806 | * 12/1993 | Sardelis et al. | 606/223 |
| 5,476,480 | * 12/1995 | Matsutani | 606/222 |
| 5,649,961 | * 7/1997 | McGregor et al. | 606/222 |

* cited by examiner

Primary Examiner—Gary Jackson

(57) ABSTRACT

The present invention relates to a suturing needle for medical use comprising a needle tip portion for piercing a body tissue, a distal end portion for coupling a suture and a body portion formed between the needle tip portion and the distal end portion The body portion is constituted of a pair of flat surfaces opposing to each other and a pair of grooves opposing to each other in a direction intersecting with the opposing direction of the flat surfaces.

1 Claim, 5 Drawing Sheets

FIG.4a(Prior Art)
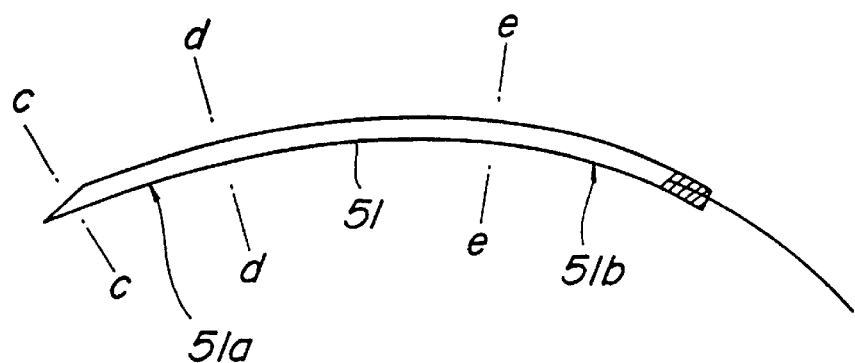
FIG.4b(Prior Art)
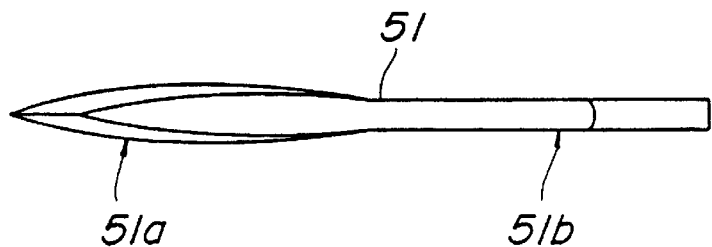
FIG.4c(Prior Art)  FIG.4d(Prior Art)  FIG.4e(Prior Art)
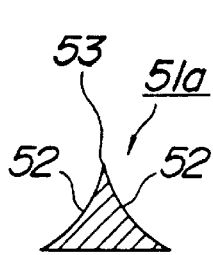 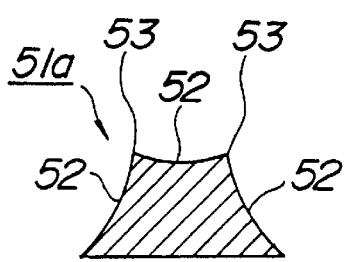 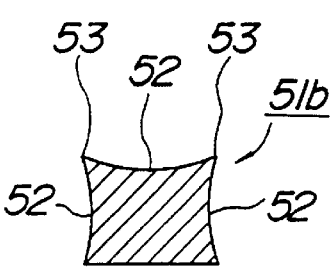

SUTURING NEEDLE FOR MEDICAL USE

BACKGROUND OF THE INVENTION

1. Field of the Invention

The present invention relates to a suturing needle for medical use having an improved bending strength and a reduced piercing resistance.

2. Description of Prior Art

Generally, a suturing needle for medical use is manipulated by a surgeon with a needle holder for clamping the needle, and the needle has a function of piercing an affected part of a body to pass a suture through the affected part. In addition, various kinds of the suturing needles for medical use with different configurations and sizes have been provided, and a suitable needle is selected among the suturing needles for medical use and is used according to the affected part to be sutured.

The suturing needle for medical use has a sharp needle tip at a tip end of the needle and has a needle tip portion formed at a predetermined distance from the needle tip, and the needle tip portion has, in sequence, a body portion and a distal end portion. A thickness of the needle tip portion has gradually increased from the sharp needle tip to the body portion, and each of the suturing needles for medical use has its own cross-sectional configuration. For example, a cross-sectional configuration of a needle tip portion may be polygonal, where a plurality of edges constituting the polygonal configuration form cutting edges; or a cross-sectional configuration may be circular with no cutting edges. The suturing needle for medical use with the cutting edge has a function of piercing a tissue with the needle tip and tearing the tissue; on the other hand, the suturing needle for medical use without the cutting edge has a function of pressingly widening the tissue to which the needle tip has pierced.

The body portion has a cross-sectional configuration extended from the cross section of the needle tip portion, or has a circular cross section, regardless of types of the cross-sectional configuration of the needle tip portion, and also the cross-sectional area of the body portion is constantly maintained. In particular, the suturing needle for medical use which even forms the cutting edge in the needle tip portion has no cutting edge in the body portion. In addition, the distal end portion is a portion to which a suture is coupled, and the distal end portion has a hole defined by a pair of hole supports having a spring property, or a blind hole formed in the distal end surface.

Specific examples of the aforementioned suturing needle for medical use will be explained. For example, a suturing needle for medical use disclosed in Japanese Unexamined Patent Publication (KOKAI) Showa No. 63-257539 is a spatulate suturing needle 51 structured for ophthalmic use as shown in FIG. 4. In the spatulate suturing needle 51, the cross section of a needle tip portion 51a is partially triangle shown in FIG. 4(c) and quadrangle shown in FIG. 4(d), and surfaces 52 constituting each of sides are formed as concave surfaces, and intersection of the above concaved surfaces forms each of ridgelines 53 as being acute. In particular, as for a portion corresponding to a body portion 51b as shown in FIG. 4(e), each of the ridgelines 53 has a highly acute angle of a cutting edge or an angle according to the cutting edge. According to the above spatulate suturing needle 51, since the acute ridgeline 53 passes through the tissue along the portion cut by the edge of the needle tip portion 51a, the portion thus injured can be reduced, and since contacting of the concave surface 52 with the tissue is reduced, the piercing resistance can be lowered.

In addition, a suturing needle 61 for medical use disclosed in Japanese Utility Model Publication (KOKAI) Showa No. 56-61212 is a needle where several convex portions 62 and concave portions 63 are alternately formed from a needle tip portion 61a toward a needle body portion 61b as shown in FIG. 5. In this art, since the convex portions 62 and the concave portions 63 are corresponded with convex portions and concave portions formed in a needle holder (not shown) to be grasped, suturing operation can be made in a stable state.

When an affected part of a human body is to be sutured by the respective suturing needle for medical use as mentioned above, the needle becomes a cantilever bar where the portion to be clamped by the needle holder is served as a supporting portion and the needle tip portion is served as a loading portion, and therefore, a large flexure is produced in the portion clamped by the needle holder, with the result that the suturing operation may suffer. However, the respective suturing needles for medical use as mentioned above do not solve such a problem, and consequently, the idea of reducing the flexure is not disclosed.

It is necessary to improve strength of the material in order to suppress the flexure generated during the suturing operation. However, when the strength of the material is improved, fragility becomes increased, causing derivatively such a problem that the material is easily folded during the suturing operation.

SUMMARY OF THE INVENTION

It is an object of the present invention to provide a suturing needle for medical use, which improves a bending strength without derogating a ductility (repetition bending strength), and further reduces a piercing resistance.

In order to achieve the aforementioned object, the present invention provides a suturing needle for medical use (hereinafter referred to simply as a "suturing needle") having a needle tip portion piercing a body tissue; a distal end portion to which a suture is coupled; and a body portion formed between the needle tip portion and the distal end portion, in which at least the body portion is constituted of a pair of surfaces opposing to each other, and a pair of grooves opposing to each other in a direction intersecting with the opposing to direction of the mentioned surfaces.

In the above suturing needle, a cross-sectional configuration of the body portion or a cross-sectional configuration from the body portion to the needle tip portion is formed by combining a pair of surfaces opposing to each other, with concave grooves formed in a direction perpendicular to the pair of surfaces. As a result, proper setting of a width size of the pair of surfaces as well as a face-to-face distance between the pair of surfaces can make a geometrical moment of inertia larger, as well as, can improve a strength with respect to bending. Consequently, when the above pair of surfaces is clamped by the needle holder for suturing an affected part of the human body, the flexure thus produced is made smaller so that a feeling of suturing operation by a surgeon is not affected.

In addition, when the aforementioned suturing needle is a curved needle having, as side surfaces, the pair of grooves, where a user manipulates a curved needle of the same kind with a snapping movement, the effect by the geometrical moment of inertia as mentioned above can be further advantageously utilized. In addition, the great advantage can be further obtained, when a relation between a width B and a height H of the cross section of the above body portion is B/H<1 where a curving direction of the mentioned suturing needle is set as a reference.

Each of the pair of surfaces opposing to each other may be a flat surface, a surface slightly convexed toward an outer periphery, or a surface slightly concaved toward the center. These surfaces are desirably formed in a process of manufacturing the suturing needle by a plastic processing, so as to increase a work hardening coefficient.

Furthermore, the suturing needle desirably has a curved surface with no edge respectively for the mentioned pair of grooves, and a curved surface for a connecting portion formed between the mentioned surface and the mentioned groove.

Since this structure results in no edge formed on the cross-sectional contour of the body portion, a portion on which tension is concentrated is hardly produced when the suturing needle is curved, thereby providing a suturing needle which is hard to be broken.

In addition, the cross-sectional contour of the above connecting portion is desirably formed by a curved line having a radius in a range from 10% to 25% of a diameter of the thickest portion of the suturing needle.

It is to be noted that the thickest portion mentioned above is a connecting portion or its vicinity between the body portion and the distal end portion in the case of the suturing needle having a blind hole in the distal end surface, or the thickest portion is a portion near the center of the body portion in the case of the suturing needle having a pair of hole supports in the distal end portion. By structuring the suturing needle as mentioned above, the pair of surfaces and the pair of the grooves respectively opposing to each other are connected by the curved surfaces having, respectively, a radius in a predetermined range, and therefore, although contacted with the pair of the surfaces through to the curved surfaces, the tissue is not contacted with the bottom portion of the groove when the affected portion is sutured. Consequently, the contacting area between the needle and the tissue is reduced, thus to be able to lower the piercing resistance.

BRIEF DESCRIPTION OF THE DRAWINGS

The above and other objects and features of the invention are apparent to those skilled in the art from the following referred embodiments thereof when considered in conjunction with the accompanied drawings, in which:

FIG. 4 is an illustration explaining a structure of the suturing needle of the first publicly known art.

DETAILED DESCRIPTION OF THE PREFERRED EMBODIMENTS

Figure 1:
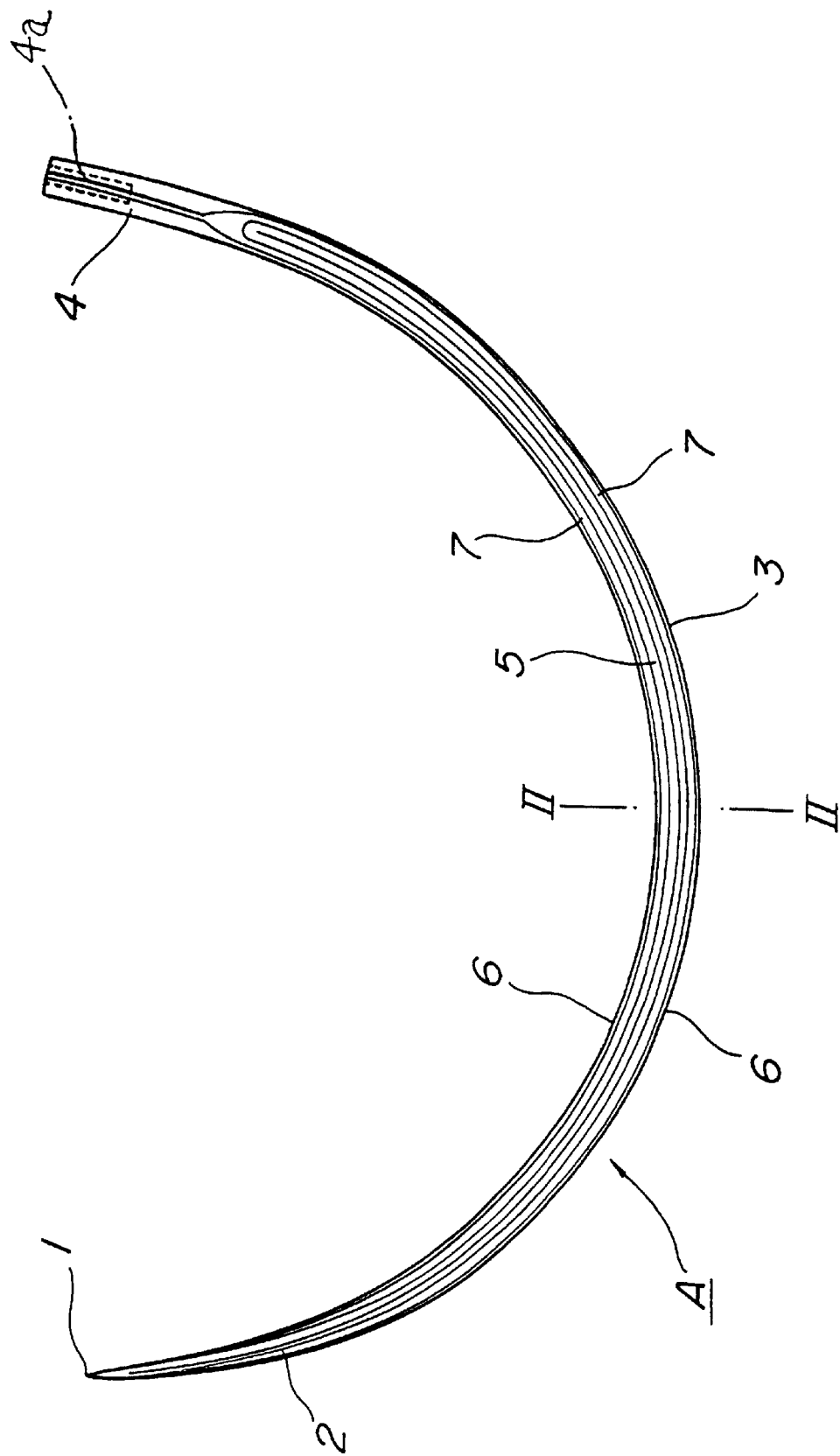
FIG. 1 is an illustration explaining a structure of a suturing needle.
Figure 2:
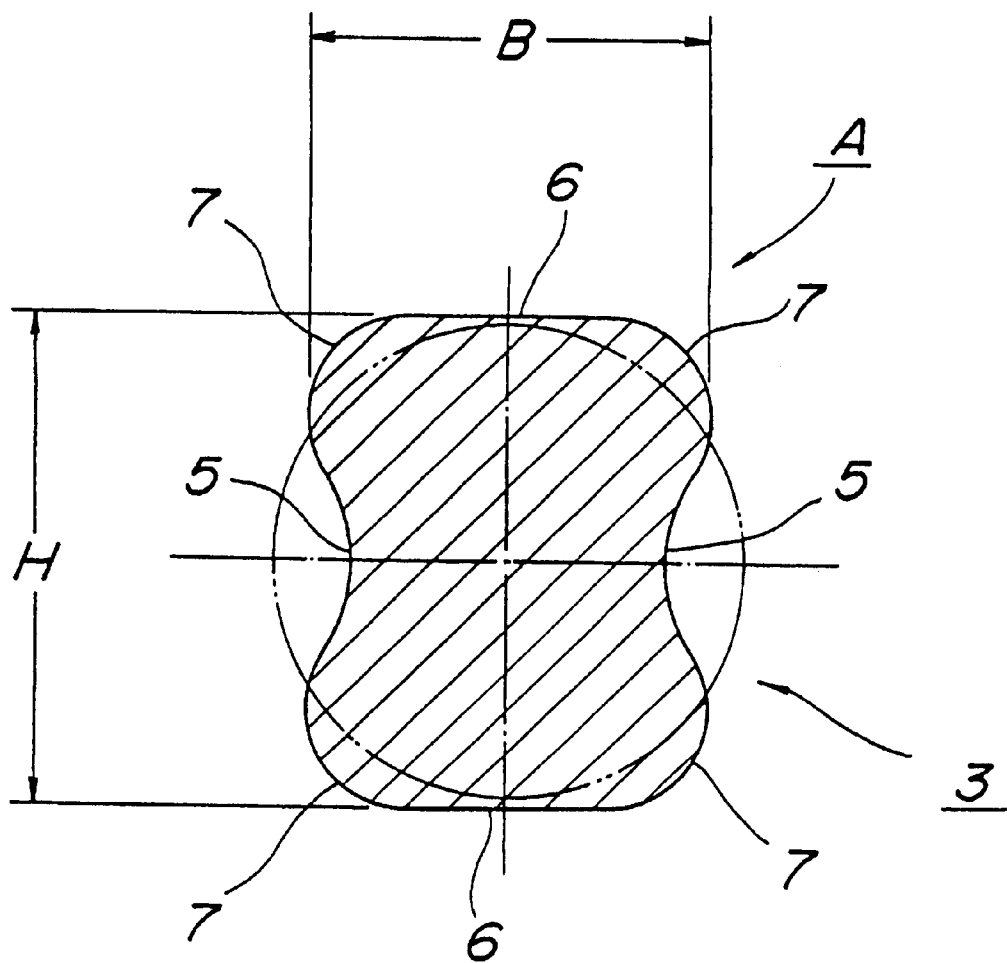
FIG. 2 is a cross-sectional view taken along line II-II in FIG. 1 for explaining a cross-sectional configuration of the body portion.

Hereinafter, explanation will be given on preferred embodiments of the above suturing needle with reference to the drawings. FIG. 1 is an illustration explaining a structure of a suturing needle. FIG. 2 is a cross-sectional view taken along line II-II in FIG. 1 for explaining a cross-sectional configuration of the body portion. FIG. 3 is an explanation view of a die used for the press working of the suturing needle.

After a tissue is first pierced by a sharp needle tip 1 of a suturing needle A shown in FIG. 1 and FIG. 2, the portion thus pierced is pressingly widen by a needle tip portion 2 formed sequentially to the needle tip 1, and while the tissue is kept in a state of being pressingly widen, a body portion 3 and a distal end portion 4 of the needle pass through the tissue, with the result that a suture (not shown) coupled to the distal end portion 4 can pass through the tissue. Thus, since the suturing needle A does not tear the tissue, the suturing needle A is used mainly for suturing blood vessels.

In particular, both the side surfaces of the body portion 3 or of the portion from the needle tip portion 2 to the body portion 3 of the suturing needle A have concave grooves 5, which can increase considerably the geometrical moment of inertia, although the body portion 3 has a cross-sectional area that is the same as that of an original circle. In addition, the suturing needle A is formed as a curved needle having a radius of curvature and a bending angle previously set with respect to the portion from the needle tip 1 through to the distal end portion 4.

The suturing needle according to the present invention, however, is not limited to the aforementioned suturing needle A (where the needle tip portion 2 has a circular cross section), and even the suturing needles having other cross-sectional configurations can be applied. In other words, such a suturing needle as forming a cutting edge at the needle tip portion can have a configuration of the body portion that is the same as that of the present embodiment, irrespective of the cross-sectional configuration of the needle tip portion. Also, the suturing needle A is not necessarily a curved needle, and a straight suturing needle can be applied.

The thickness of the suturing needle is typically in a range from 0.025 mm to 1.40 mm, and the suturing needle having the mentioned thickness is selected and utilized by the surgeon according to the portions to be sutured. Thus, as the suturing needle A, for example, for suturing the blood vessel as that in the present embodiment, there are a variety of the suturing needles A, to be employed, having different diametral thicknesses according to the diametral thickness and the thickness of the blood vessel to be sutured, different radii of curvature, and different bending angles.

The needle tip portion 2, formed as a conical-shaped taper along the portion from the needle tip 1 to the body portion 3, has a function of pressingly widening the tissue to which the needle tip 1 has pierced, without tearing the tissue, and the needle tip portion 2 has a circular cross section in sequence from the sharp needle tip 1 formed at the tip end, or a Japanese drum-shape cross section explained below, mentioned later, from the vicinity of the body portion 3 to the body portion, in which the cross-sectional area increases as the distance from the needle tip 1 increases.

The body portion 3 is a portion clamped by the needle holder (not shown) in a stable state when the affected part is to be sutured, where the cross-sectional configuration has a drum shape in which the upper portion projects laterally; the middle portion recedes; and the lower portion again projects laterally, as shown in FIG. 2. The cross-sectional area of the body portion is maintained approximately at a predetermined value even when the distance from the needle tip 1 is changed.

The distal end portion 4 has a function of coupling a suture (not shown) thereto, where, after an end of the suture is inserted into a blind hole formed in a predetermined depth from the end surface side, the suture can be coupled thereto by caulking the circumference of the blind hole, or the suture can be coupled to the distal end portion 4 by a hook-shaped slip stopper piece formed at a position opposite to a pair of protruding hole supports having a spring property. In the present embodiment, the suturing needle A is formed as a so-called eyeless needle forming a blind hole 4a in the end surface of the distal end portion 4.

Next, the cross-sectional configuration of the body portion 3 will be specifically explained. The body portion 3 has, as a pair of flat surfaces 6, surfaces opposing to each other formed respectively on an inside diameter side and an outside diameter side of the curvature, and has, as a pair of concave grooves 5, both of the side surfaces of the curvature, each of the side surfaces being concaved toward the center of the body portion 3. In addition, a connecting portion 7 between the flat surface 6 and the groove 5 is formed by a curved surface having a radius in a range from 10% to 25% of a diameter of the thickest portion of the suturing needle A, and the connecting portion 7 connects smoothly the flat surface 6 to the groove 5 consisting of the concave surface, so as to make the whole structure a shape similar to a shoulder drum (drum shape).

Forming each of the surfaces opposing to each other as flat face 6, a needle holder can hold the suturing needle with good stability.

The connecting portion 7 between the flat surface 6 and the groove 5 is not necessarily a curved surface, but may be formed in a polygonal shape consisting of a lot of straight lines sequentially provided. Also in this case, the apparent radius of curvature of the polygonal shape is preferably in a range from 10% to 25% of a diameter of the thickest portion of the suturing needle A.

Regarding the above drum-shaped cross section of the body portion 3, the cross-sectional area is not changed along the whole length of the body portion 3, and is a value approximately the same as that of the material constituting the suturing needle A. A ratio of the width size B of the flat surface 6 to the distance H (height size) between the flat surfaces 6 is not especially limited, but the ratio of B to H (B/H) is preferably 1 or less. The ratio of 1 or less can make the value of the geometrical moment of inertia larger. Also the ratio of B to H (B/H) is equals to 0.7 or more. If the ratio is less than 0.7, the suturing needle lacks stability when it is held with the needle holder.

Consequently, when the cross section of a material used for constituting the suturing needle A is in a circular shape, the width size B of the flat surface 6 is set smaller than a diameter of the circle, while the height size H is set larger than the diameter of the circle. When the drum shape of the body portion 3 is to be formed, in particular, it is preferred not to eliminate the material, but to employ a plastic processing without depending on the cutting processing. Thus, due to that the body portion 3 is formed by the plastic processing, the material can be used effectively so as to form a rationalized cross-sectional shape.

In the case of forming the groove 5 by using the plastic processing, increasing the depth of the groove 5 leads to a high hardness of the material. However, higher hardness of the material prevents the material from being flexible, meaning that the material becomes easily folded. As a result, there is some limit for the depth of the groove 5, and the groove cannot be deeper without limitation. The shape of the groove 5 includes a V shape with a gentle bottom surface, an arc shape or the like, and when the arc shape is used, the radius of curvature is preferably around 15% to 45% of a diameter of the thickest portion of the suturing needle A.

According to the present invention, for example, a diameter of the thickest portion is 0.45 mm; a width size B of the flat surface 6 and a height H between the flat surfaces 6 are respectively set 0.381 mm and 0.470 mm; and the radius of curvature of the groove 5 is 0.150 mm. Then, each of the grooves 5 having the aforementioned radius of curvature and each of the flat surfaces 6, together with the respective connecting portions 7 having curved surfaces with various kinds of the radii of curvature, become test pieces which were used for piercing tests and bending tests.

According to the result of the tests mentioned above, good result is obtained, when the radius of curvature of the connecting portion 7 is in a range from 10% to 25% of a thickness of the thickest portion of the suturing needle A (a connecting portion between the body portion 3 and the distal end portion 4, and the vicinity of the portion). In other words, when the radius of curvature of the connecting portion 7 is smaller than the range mentioned above, the connecting portion 7 becomes sharp, with the result that deformations are concentrated so that the connecting portion 7 is easily folded when the needle is bent; on the other hand, when the radius of curvature of the connecting portion 7 becomes larger than the range mentioned above, the size of the groove 5 becomes smaller so that the contacting of the groove with the tissue increases, with the result that reduction of the piercing resistance becomes difficult.

Since the tissue does not contact with the groove 5 formed in the body portion 3 when the aforementioned suturing needle A pierces an affected part of the human body, a piercing resistance becomes lowered. For example, when compared with a conventional needle having a body portion with a circular cross section and a thickness that is the same as that of the suturing needle A, the suturing needle A of the present embodiment had a piercing resistance of 100 g, while the conventional suturing needle had a piercing resistance of 110 g. These values show that a piercing resistance is sufficiently lowered as a suturing needle which has such a configuration as making it difficult to reduce the piercing resistance and as not tearing the tissue.

The result of bending tests using the suturing needle A of the present embodiment shows that the suturing needle A was able to improve the strength approximately 1.4 times the strength of the conventional needle having a body portion with a circular cross section as well as having the value of the thickest portion which is the same as that of the suturing needle A. In addition, the result of 90-degree bending tests, where the needle is repeatedly bent at a 90 degree in the direction of an outside diameter of the curvature, shows that the suturing needle A was able to endure the number of bending times (three times) which is the same as that of the needle having a body portion with a circular cross section as well as having the value of the thickest portion which is the same as that of the suturing needle.

These results mean the improvement of the bending strength while still having a ductility (repetition bending strength) which is the same as that of the conventional round needle.

In particular, as seen from the observation of the motion during the 90-degree bending tests, it was found that, as the body portion 3 was clamped by a vise to become bent, deformation of the flat surface 6 was concentrated on the connecting portion 7 having a curved surface of the body portion 3 on the inner side of the curvature, while deformation of the flat surface 6 was concentrated on the groove 5 on the outer side of the curvature. It is considered that this resulted in the improvement of the ductility. For instance, when the 90-degree bending test was conducted with respect to a suturing needle having a rectangular cross section where a width B of the flat surface and a distance H between the flat surfaces were set to be the same as those of the needle of the present embodiment, the suturing needle was fractured by second time of the bending operation. This also indicates that the needle is required to have each of the flat surfaces 6 opposing to each other as well as a pair of the concave grooves 5, and is required to connect these surfaces to the grooves through the connecting portion 7 formed of a curved surface.

A process for manufacturing the above suturing needle A will be described.

The suturing needle A is required to have a sufficient hardness and to be prevented from having rust and corrosion, in order to pierce the tissue when suturing the affected part. Consequently, in the present embodiment, an austenitic stainless steel is used as a material, where a wire material having a diameter previously set in consideration of the processing rate is subjected to a cold wiredrawing processing, and then the diameter is reduced to obtain a desired diameter of the suturing needle A.

The wire thus obtained according to the step mentioned above has fibrously extended austenitic texture in the material, and therefore the wire can gain a high hardness due to work hardening and a high flexibility due to the fibrous texture. In particular, since the austenitic stainless steel is used for the material, the material can be prevented from having rust because a high anti-corrosive property is provided, and also the material can be adequately flexible.

The above material is cut to have a desired length of the suturing needle A, and is processed to be a straight material. One of the end portions of the material is polished to form the needle tip 1 and the needle tip portion 2 of a conical shaped taper.

Figure 3A:
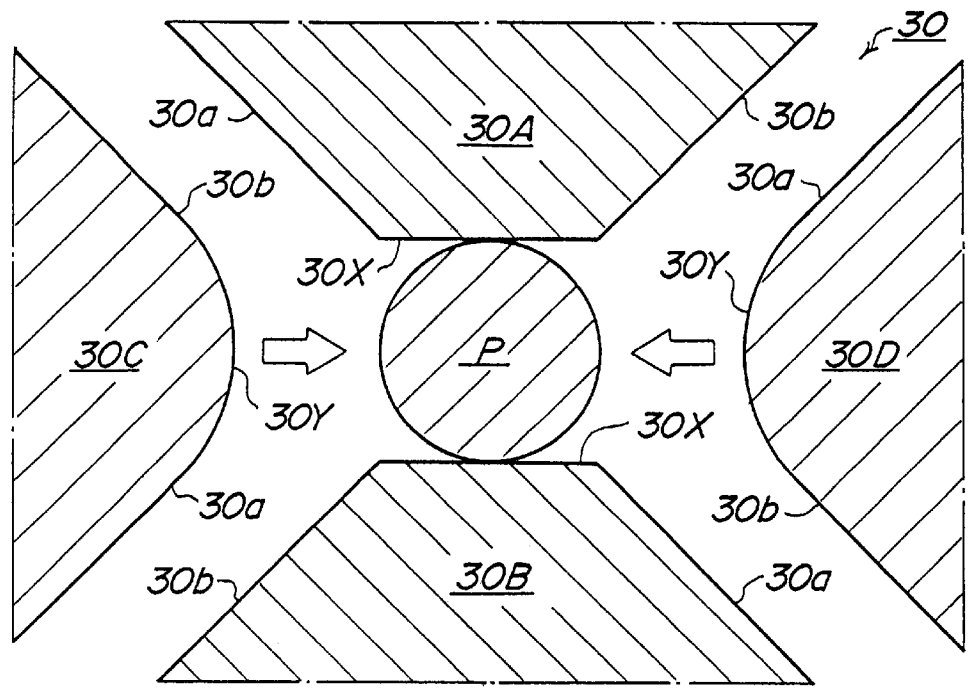
FIG. 3 is an explanation view of a die used for the press working of the suturing needle.
Figure 3B:
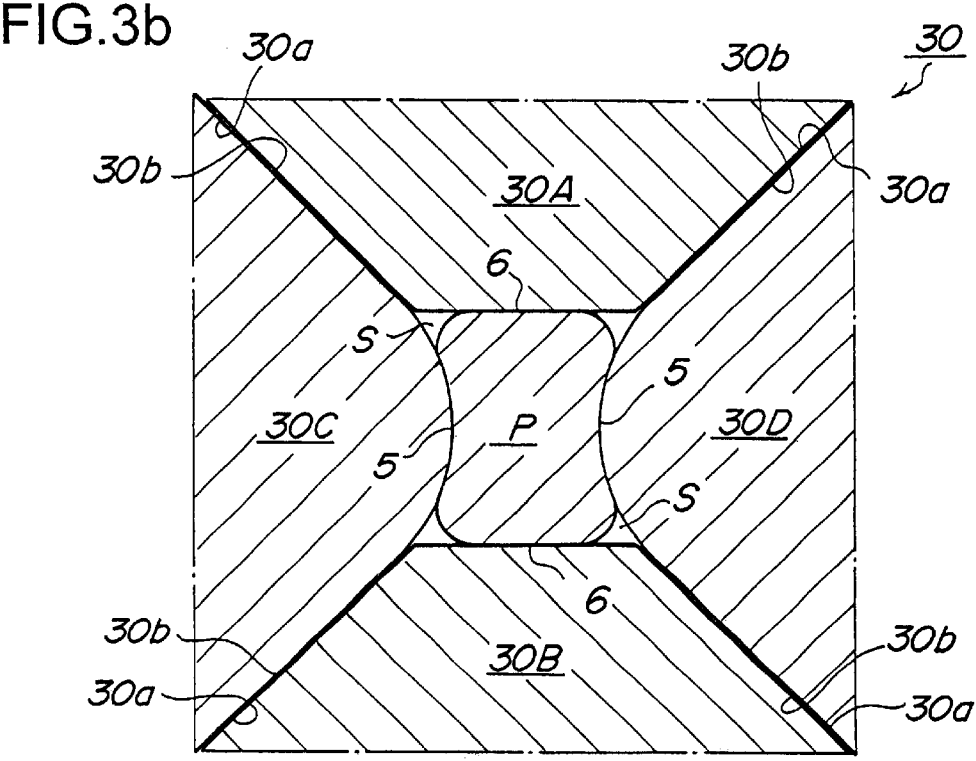
Figure 5A:
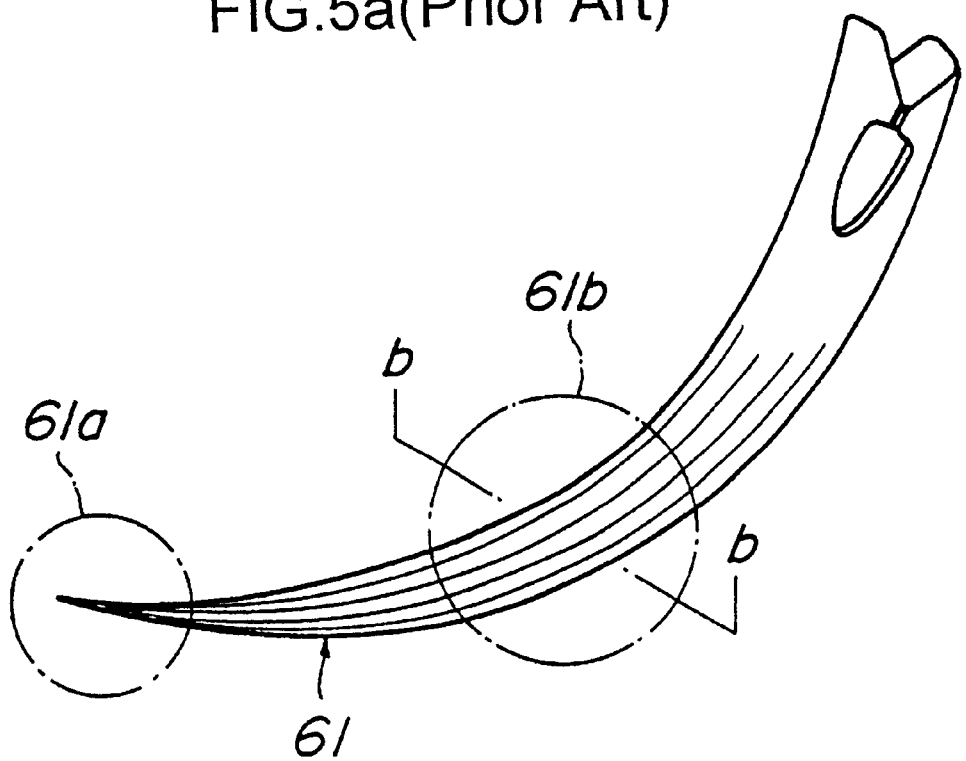
FIG. 5 is an illustration explaining a structure of the suturing needle of the second publicly known art.
Figure 5B:
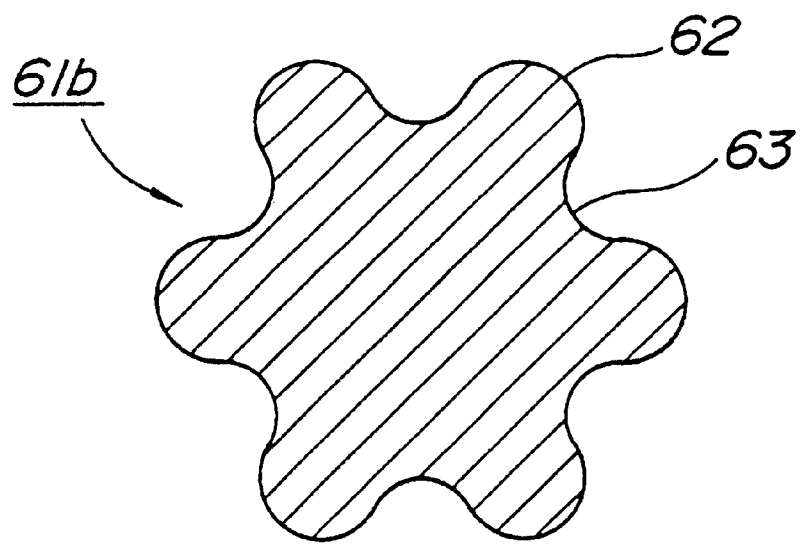

Next, a press step for an intermediate material subjected to cold wiredrawn is shown in FIG. 3. As shown in FIG. 3(a), the press step utilizes a press die 30 including divided 4 pieces. The press die 30 consists of a top piece 30A, a bottom piece 30B, a left piece 30C and a right piece 30D, each having a shape where a cross section has an approximately triangle tip constituted of two lines 30a, 30b which intersect at a 90 degree.

The tip end of each of the top piece 30A and the bottom piece 30B has a flat surface portion 30X, while the tip end of each of the left piece 30C and right piece 30D has respectively a projecting portion 30Y having a shape of circular arc. When these four pieces, 30A, 30B, 30C, and 30D are set up, the adjacent lines of 30a, 30b of the respective dies are joined to form, in the center, a space S having flat top and bottom surfaces and concave side surfaces (See, FIG. 3(b)).

Among the pieces 30, the top piece 30A and the bottom piece 30B are used to sandwich and hold, vertically, the intermediate material P with both the flat surface portions of the pieces thus used, so as not to move the intermediate material P. When the left piece 30C and the right piece 30D are moved laterally, the respective projecting portions 30Y in a circular arc shape push the intermediate material P to deform the cross sectional configuration of the intermediate material P. The intermediate material P, thus deforming along the configuration of the space S, is then formed as a suturing needle having flat surfaces 6 on the top and bottom surfaces and grooves 5 on the left and right side surfaces.

It is to be noted that, since the press die 30 is constituted of the piece 30A, 30B, 30C and 30D each having the configuration mentioned above, when the pieces 30A, 30B, 30C, and 30D are respectively subjected to the mold clamping, applying forces from the four sides are balanced on the lines 30a, 30b adjacent between the respective pieces 30A, 30B, 30C and 30D, and pushing force of the projecting portions 30Y are constantly maintained. Thus, stable deforming processing can be constantly performed with respect to the intermediate material P without pressing excessive force thereto.

Following, or preceding the above processing, the distal end portion 4 is formed at an end portion on the other side of the above needle portion. That is, the end surface on the other side of the needle portion of the material is melted by radiation of laser light, and is then evaporated to form the blind hole 4a, or the end surface is subjected to drill processing to form the blind hole 4a, thereby forming the distal end portion 4 at the end portion.

After the needle tip 1, the needle tip portion 2, the body portion 3, the distal end portion 4, the groove 5, the flat surface 6, and the connecting portion 7 are formed, the flat surfaces 6 are disposed respectively on the side of the inside, diameter and on the side of the outside diameter of the curvature, and then are subjected to a bending molding to curve for obtaining the desired radius of curvature and angle of the suturing needle A, thereby producing the suturing needle A.

A portion from the needle tip 1 to the body portion 3 of the suturing needle A thus obtained is a fibrously extended austenitic texture, thereby having a high hardness and a high flexibility. As a result, tissue of the affected part can be pierced extremely easily in suturing the affected part.

It is to be noted that, although the suturing needle for medical use of the present invention is explained as a curved needle according to the present embodiment, the suturing needle A for medical use having the grooves 5 on the both side surfaces and the flat surfaces 6 on the top and bottom surfaces has a smaller contacting area with the body tissue, thereby obtaining such an effect as reducing the piercing resistance; as a result, when applying to a straight needle which is not curved, the suturing needle can gain the given effect.

In addition, the aforementioned embodiment is explained as a suturing needle for medical use having the flat surfaces 6 on the top and bottom surfaces, but the suturing needle for medical use according to the present invention is not limited to this; a suturing needle having curved surfaces on the top and bottom surfaces may be used. It is to be noted that, although the configuration of the groove 5 may be a V-shaped type, a rectangularly letter U-shaped type or other type in various shapes, a groove which does not form edges as shown in the present embodiment can provide a high ductility.

Furthermore, although the groove 5 is formed in a portion from the body portion 3 to the needle tip portion 2 according to the present embodiment, such a structure as having the groove only in the body portion 3 may be used.

Since the body portion of the suturing needle according to the present invention is constituted of a pair of surfaces opposing to each other, as well as, a pair of grooves concaved toward the center in which the groove intersects with the surface, when the pair of the surfaces are disposed on the top and bottom sides, a value of the geometrical moment of inertia becomes large, thus to be able to show a high strength with respect to bending movement. In particular, the groove is formed in a shape concaved toward the center of the body portion, the contacting area with the body tissue can be smaller during the piercing operation, thereby achieving in reducing the piecing resistance.

In addition, since the pair of the surfaces and the pair of the grooves are connected by the curved surface having a value of the radius of curvature in a range from 10% to 25% of a diameter of the thickest portion of the suturing needle, concentration of the bending stress is not given, thereby achieving a strong suturing needle with respect to bending movements.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A suturing needle for medical use comprising:

a needle tip portion for piercing a body tissue;

a distal end portion for coupling a suture; and a body portion formed between the needle tip portion and the distal end portion having a cross section, a width B of the cross section and a height H of the cross section, wherein at least the body portion comprises a pair of flat surfaces opposing each other, a pair of grooves opposing each other in a direction intersecting with the opposing direction of the flat surfaces, and a relation of the body portion B/H such that $0.7<B/H<1$, where a curving direction of the suturing needle is set as a reference.

* * * * *